United States Patent [19]

Holderbaum et al.

[11] Patent Number: 5,443,820

[45] Date of Patent: Aug. 22, 1995

[54] ESTERS AND AMIDES OF AMINOMETHYLENECYANOACETIC ACID A COSMETIC PREPARATION CONTAINING THE SAME AS A SUNSCREEN AGENT AND A METHOD FOR PROTECTING HUMAN SKIN USING THE SAME

[75] Inventors: Martin Holderbaum, Ludwigshafen; Alexander Aumueller, Neustadt; Hubert Trauth, Dudenhofen, all of Germany

[73] Assignee: Basf Aktiengesellschaft, Ludwigshafen, Germany

[21] Appl. No.: 170,314

[22] PCT Filed: Jun. 25, 1992

[86] PCT No.: PCT/EP92/01432

§ 371 Date: Jan. 5, 1994

§ 102(e) Date: Jan. 5, 1994

[87] PCT Pub. No.: WO93/01164

PCT Pub. Date: Jan. 21, 1993

[30] Foreign Application Priority Data

Jul. 6, 1991 [DE] Germany .................. 41 22 475.2

[51] Int. Cl.⁶ .................. A61K 7/42; C07D 239/42; C07D 213/72; C07C 255/09
[52] U.S. Cl. .................. 424/59; 424/60; 424/401; 544/296; 544/330; 544/331; 544/332; 546/225; 546/264; 546/266; 546/287; 546/304; 546/307; 558/393; 558/394; 558/395; 558/398; 558/400
[58] Field of Search .................. 424/59, 401, 60; 544/296, 330, 331, 332; 546/255, 264, 266, 287, 304, 307; 558/393, 394, 398, 395, 400

[56] References Cited

U.S. PATENT DOCUMENTS 3,079,366 2/1963 Boyle et al. .................. 558/394
4,218,515 8/1980 Heckles .................. 428/474
5,155,152 10/1992 Wehner et al. .................. 524/100

FOREIGN PATENT DOCUMENTS 3825382 2/1989 Germany .

*Primary Examiner*—Yogendra N. Gupta
*Attorney, Agent, or Firm*—Oblon, Spivak, McClelland, Maier & Neustadt

[57] ABSTRACT

Esters and amides of aminomethylenecyanoacetic acid I

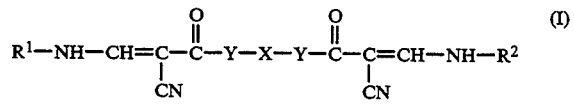

where
$R^1$ and $R^2$ are each, independently of one another, phenyl, naphthyl, biphenylyl or five- or six-membered hetaryl with one, two or three nitrogens or one oxygen or one sulfur or one nitrogen and one oxygen or one nitrogen and one sulfur, which can be benzo-fused, it being possible for these radicals to be substituted by one to three $C_1$–$C_{12}$-alkyl groups, $C_1$–$C_{12}$-alkoxy groups, halogen atoms, cyano groups, hydroxyl groups or groups of the formulae $COOR^3$, $COR^3$, $CONHR^3$, $OCOR^3$ or $NHCOR^3$, and where
$R^3$ is $C_1$–$C_{12}$-alkyl, $C_5$–$C_8$-cycloalkyl or phenyl,
X is $C_2$–$C_{30}$-alkylene which can be interrupted by non-adjacent oxygens, or is $C_4$–$C_{12}$-alkenylene or $C_4$–$C_{12}$-alkynylene where the unsaturated bonds are not adjacent to the ester oxygens, or is $C_5$–$C_8$-cycloalkylene or phenylene, and
Y is O or NH.

are used as stabilizers for organic materials.

8 Claims, No Drawings

ESTERS AND AMIDES OF AMINOMETHYLENECYANOACETIC ACID A COSMETIC PREPARATION CONTAINING THE SAME AS A SUNSCREEN AGENT AND A METHOD FOR PROTECTING HUMAN SKIN USING THE SAME

This application is a 371 of PCT/EP92/01432 filed on Jun. 25, 1992.

The present invention relates to novel esters and amides of aminomethylenecyanoacetic acid of the formula I

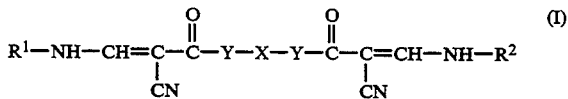

where
- $R^1$ and $R^2$ are each, independently of one another, phenyl, naphthyl, biphenylyl or five- or six-membered hetaryl with one, two or three nitrogens or one oxygen or one sulfur or one nitrogen and one oxygen or one nitrogen and one sulfur, which can be benzo-fused, it being possible for these radicals to be substituted by one to three $C_1$–$C_{12}$-alkyl groups, $C_1$–$C_{12}$-alkoxy groups, halogen atoms, cyano groups, hydroxyl groups or groups of the formulae $COOR^3$, $COR^3$, $CONHR^3$, $OCOR^3$ or $NHCOR^3$, and where
- $R^3$ is $C_1$–$C_{12}$-alkyl, $C_5$–$C_8$-cycloalkyl or phenyl,
- X is $C_2$–$C_{30}$-alkylene which can be interrupted by non-adjacent oxygens, or is $C_4$–$C_{12}$-alkenylene or $C_4$–$C_{12}$-alkynylene where the unsaturated bonds are not adjacent to the ester oxygens, or is $C_5$–$C_8$-cycloalkylene or phenylene, and
- Y is O or NH.

The present invention also relates to a process for preparing the compounds I and to organic materials containing the compounds I and thus stabilized against the action of light, oxygen and heat, especially stabilized plastics and surface coatings, and to cosmetic preparations containing the compounds I as sunscreen agents.

Organic materials, especially plastics and surface coatings, are known to be very rapidly decomposed in particular by the action of light. This decomposition is normally manifested by yellowing, discoloration, fissuring or embrittlement of the material. No satisfactory protection against decomposition of organic material by light, oxygen and heat has been achieved with the stabilizers used to date.

Thus, for example, U.S. Pat. No. 3,079,366 recommends, inter alia, arylaminoethylenes of the formula III

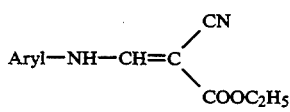

as UV absorbers for plastics. Although the compounds III have the required spectroscopic properties, they do not meet current requirements in terms of their stabilizing action. In particular, the tendency of plastics stabilized with the compounds III to become yellow is still too great.

It is an object of the present invention to provide stabilizers which effectively protect organic material.

We have found that this object is achieved by the esters and amides of aminomethylenecyanoacetic acid I defined in the first paragraph.

Examples of suitable hetaryl radicals $R^1$ and $R^2$ are those derived from pyrrole, pyrazole, imidazole, 1,2,3-triazole, 1,2,4-triazole, pyridine, pyridazine, pyrimidine, pyrazine, 1,2,3-triazine, 1,2,4-triazine, 1,2,3-triazine, furan, thiophene, oxazole, isoxazole, thiazole, indole, benzofuran, benzothiophene, benzimidazole, quinoline, isoquinoline, cinnoline, quinazoline, quinoxaline or phthalazine.

Suitable substituents on the ayrl or hetaryl radicals $R^1$ and $R^2$ are:
- straight-chain or branched $C_1$–$C_{12}$-alkyl such as, in particular, methyl, ethyl, n-propyl, isopropyl, n-butyl, isobutyl, sec-butyl and tert-butyl, but also n-pentyl, tert-pentyl, n-hexyl, n-heptyl, n-octyl, 2-ethylhexyl, n-nonyl, isononyl, n-decyl, isodecyl, n-undecyl or n-dodecyl;
- straight-chain or branched $C_1$–$C_{12}$-alkoxy such as, in particular, methoxy, ethoxy, n-propoxy, isopropoxy, n-butoxy, isobutoxy, sec-butoxy, n-pentoxy and tert-pentoxy, but also n-hexoxy, n-heptoxy, n-octoxy, 2-ethylhexoxy, n-nonoxy, isononoxy, n-decyloxy, isodecyloxy, n-undecyloxy or n-dodecyloxy;
- halogen such as, in particular, chlorine, but also fluorine, bromine or iodine;
- cyano;
- hydroxyl;
- groups of the formula $COOR^3$, for example methoxycarbonyl, ethoxycarbonyl, propoxycarbonyl or butoxycarbonyl;
- groups of the formula $COR^3$, for example acetyl or benzoyl;
- groups of the formula $CONHR^3$, for example N-methyl-aminocarbonyl, N-ethylaminocarbonyl or N-phenylaminocarbonyl;
- groups of the formula $OCOR^3$, for example methoxycarbonyloxy or ethoxycarbonyloxy;
- groups of the formula $NHCOR^3$, for example N-acetylamino, N-propionylamino or N-benzoylamino.

In these groups, $R^3$ is straight-chain or branched $C_1$–$C_{12}$-alkyl, for which the same examples as indicated above can be given, $C_5$–$C_8$-cycloalkyl such as, in particular, cyclopentyl and cyclohexyl, but also cycloheptyl, cyclooctyl, methylcyclopentyl, dimethylcyclopentyl, methylcyclohexyl or dimethylcyclohexyl, and phenyl.

The number of substituents on the aryl or hetaryl radicals $R^1$ and $R^2$ can be up to 3, preferably up to 2. Where there are several substituents, these can be identical or different.

In a preferred embodiment, $R^1$ and $R^2$ are each, independently of one another, in particular phenyl which can be substituted by one or two $C_1$–$C_{12}$-alkyl groups, in particular $C_1$–$C_4$-alkyl groups, $C_1$–$C_{12}$-alkoxy groups, in particular $C_1$–$C_5$-alkoxy groups, chlorine atoms, cyano groups, hydroxyl groups or groups of the formula $COOR^3$ where $R^3$ has the abovementioned meanings, but especially $C_1$–$C_4$-alkyl, cyclopentyl, cyclohexyl or phenyl, but also pyridinyl or 2-pyrimidinyl, each of which can be substituted by one or two $C_1$–$C_4$-alkyl groups, especially methyl or ethyl.

Suitable bridges X are:

straight-chain or branched $C_2$–$C_{30}$-alkylene such as 1,2-ethylene, 1,2-propylene, 1,3-propylene, 1,4-butylene, 1,2-butylene, 2,3-butylene, pentamethylene, hexamethylene, heptamethylene, octamethylene, nonamethylene, decamethylene, undecamethylene or dodecamethylene;

$C_2$–$C_{30}$-alkylene, in particular $C_2$–$C_{18}$-alkylene, which is interrupted by one or up to 9, in particular one or up to 5, non-adjacent oxygens and is preferably straight-chain or branched to only a small extent;

$C_4$–$C_{12}$-alkenylene such as 1,4-but-2-enylene, 1,6-hex-3-enylene or 1,8-oct-4-enylene;

$C_4$–$C_{12}$-alkynylene such as 1,4-but-2-ynylene, 1,6-hex-3-ynylene or 1,8-oct-4-ynylene;

$C_5$–$C_8$-cycloalkylene such as 1,3-cyclopentylene, 1,2-cyclohexylene, 1,3-cyclohexylene, 1,4-cyclohexylene, 1,4-cycloheptylene, 1,5-cyclooctylene or

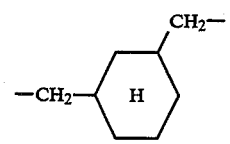

or

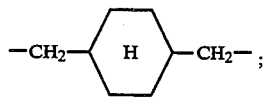

o-, m- or, in particular, p-phenylene.

In a preferred embodiment, the bridge X is $C_2$–$C_{12}$-alkylene, in particular $C_2$–$C_6$-alkylene, which is preferably polymethylene;

a polyethylene glycol or polypropylene glycol group of the formula —$(CH_2CH_2O)_n$—$CH_2CH_2$— or

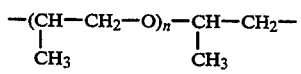

where n is 1 to 9, in particular 1 to 5 (the values for n are usually averages);

cis-1,4-but-2-enylene;

1,4-but-2-ynylene;

$C_6$–$C_8$-cycloalkylene, in particular 1,2-cyclohexylene or 1,4-cyclohexylene or

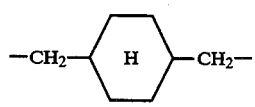

p-phenylene.

The compounds I are advantageously prepared by reacting esters or amides of cyanoacetic acid of the formula II

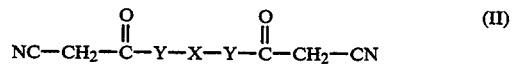

where X and Y have the abovementioned meanings, with 2 equivalents of aromatic or heteroaromatic amines of the formula $R^1$—$NH_2$ or $R^2$—$NH_2$, where $R^1$ and $R^2$ have the abovementioned meanings, and at least 2 equivalents of a trialkyl orthoformate.

Suitable trialkyl orthoformates are trimethyl orthoformate and, in particular, triethyl orthoformate.

The reaction is expediently carried out in a suitable polar organic solvent such as an alcohol, eg. n-propanol, n-butanol, ethylene glycol, diethylene glycol, ethylene glycol monomethyl ether, cyclohexanol or similar compounds. Also suitable as solvents are carboxamides such as dimethylformamide or excess trialkyl orthoformate. If the starting compounds form a liquid mixture it is possible to dispense with an additional solvent.

The reaction is usually carried out at from 70° to 180° C., preferably 100° to 150° C., under atmospheric pressure. The three reactants are used in the stated stoichiometric or approximately stoichiometric ratio if the trialkyl orthoformate is not also used as solvent; a slight excess of one of the reactants, say up to about 15%, is acceptable.

If the reaction times are very long it is possible to add as catalysts if required Lewis acids such as $AlCl_3$, $ZrCl_4$, $TiCl_4$ or, in particular, $ZnCl_2$ in the amounts customary for this purpose.

The cyanoacetic esters II can be prepared, for example, by reacting cyanoacetic acid with appropriate diols HO—X—OH in the presence of a catalyst such as boric acid or tetrabutyl orthotitanate, and they are disclosed, for example, in U.S. Pat. No. 4,218,515 and EP-A 136 260.

The esters and amides of aminomethylenecyanoacetic acid I according to the invention are outstandingly suitable as stabilizers of organic material against the action of light, oxygen and heat. They are also effective metal deactivators. They are added to the organic material to be stabilized in a concentration of from 0.01 to 5%, preferably from 0.02 to 2%, of the weight of the organic material, before, during or after its production.

Examples of organic materials are cosmetic products such as ointments and lotions, pharmaceutical formulations such as pills and suppositories, or precursors for plastics and surface coatings, but in particular plastics and surface coatings themselves.

The present invention also relates to organic material, in articular plastics and surface coatings, which is stabilized against the action of light, oxygen and heat and contains the compounds I in the concentrations stated above.

All conventional apparatus and methods for mixing stabilizers or other additives with polymers can be used for mixing the compounds I according to the invention in particular with plastics.

The organic material stabilized by the compounds I according to the invention may contain further additives, eg. antioxidants, light stabilizers, metal deactivators, antistatic agents, flameproofing agents, pigments and fillers.

Examples of antioxidants and light stabilizers which can be used in addition to the compounds according to the invention are compounds based on sterically hindered phenols or sulfur- or phosphorus-containing costabilizers.

Examples of phenolic antioxidants are 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, tris(3,5-di-tert-butyl-4-hydroxybenzyl) isocyanurate, tris[β-(3,5-di-tert-butyl-4-hydroxyphenyl) propionylethyl] isocyanurate, tris(2,6-dimethyl-3-hydroxy-4-tert-butylbenzyl) isocyanurate and pentaerythritol tetrakis [β-(3,5-di-tert-butyl-4-hydroxyphenyl)propionate].

Examples of suitable phosphorus-containing antioxidants are tris(nonylphenyl) phosphite, distearyl pentaerythritol diphosphite, tris(2,4-di-tert-butylphenyl) phosphite, tris(2-tert-butyl-4-methylphenyl) phosphite, bis(2,4-di-tert-butylphenyl) pentaerythritol diphosphite and tetrakis(2,4-di-tert-butylphenyl) 4,4'-biphenylene diphosphite.

Examples of suitable sulfur-containing antioxidants are dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Examples of other antioxidants and light stabilizers which can be used together with the compounds I are (2-(2-hydroxyphenyl)benzotriazoles, 2-hydroxybenzophenones, aryl esters of hydroxybenzoic acids, α-cyanocinnamic acid derivatives, benzimidazolecarboxanilides, nickel compounds or oxalic acid dianilides.

Particularly good stabilization is obtained when at least one light stabilizer from the class of sterically hindered amines is also added in the usual concentration to the compounds I. Examples of suitable sterically hindered amines are bis(2,2,6,6-tetramethylpiperidyl) sebacate, bis(1,2,2,6,6-pentamethylpiperidyl) sebacate, bis(1,2,2,6,6-pentamethylpiperidyl) esters, the condensation product of 1-hydroxyethyl-2,2,6,6-tetramethyl-4-hydroxypiperidine and succinic acid, the condensation product of N,N'-(2,2,6,6-tetramethylpiperidyl) hexamethylenediamine and 4-tert-octylamino-2,6-dichloro-1,3,5-triazine, tris(2,2,6,6-tetramethylpiperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone), and the condensation products of 4-amino-2,2,6,6-tetramethylpiperidines and tetramethylolacetylenediureas.

Examples of plastics which can be stabilized by the compounds I according to the invention are:

polymers of mono- and diolefins such as low or high density polyethylene, polypropylene, linear poly-1-butene, polyisoprene, polybutadiene and copolymers of mono- or diolefins or mixtures of said polymers; copolymers of mono- or diolefins with other vinyl monomers such as ethylene/alkyl acrylate copolymers, ethylene/alkyl methacrylate copolymers, ethylene/vinyl acetate copolymers or ethylene/acrylic acid copolymers;

polystyrene;

copolymers of styrene or α-methylstyrene with dienes and/or acrylic derivatives such as styrene/butadiene, styrene/acrylonitrile (SAN), styrene/ethyl methacrylate, styrene/butadiene/ethyl acrylate, styrene/acrylonitrile/methacrylate, acrylonitrile/butadiene/styrene (ABS) or methyl methacrylate/butadiene/styrene (MBS);

halogen-containing polymers such as polyvinyl chloride, polyvinyl fluoride, polyvinylidene fluoride and copolymers thereof;

polymers which are derived from α,β-unsaturated acids and derivatives thereof, such as polyacrylates, polymethacrylates, polyacrylamides and polyacrylonitriles;

polymers derived from unsaturated alcohols and amines or the acrylic derivatives or acetals thereof, eg. polyvinyl alcohol and polyvinyl acetate;

polyurethanes, polyamides, polyureas, polyesters, polycarbonates, polysulfones, polyether-sulfones and polyether-ketones.

The compounds I according to the invention can also be used to stabilize surface coatings, eg. industrial coatings. Particularly emphasized among these are stoving enamels, and among these in turn automobile coatings, preferably two-layer coatings.

The compounds I can be added in solid or dissolved form to the coating agent. Their good solubility in coating systems is a particular advantage in this connection.

It is also possible when they are used as stabilizers in surface coatings to use the additional additives mentioned above, especially antioxidants and light stabilizers.

The compounds I according to the invention are particularly suitable for the stabilization of polystyrene, copolymers of styrene and acrylonitrile (SAN) and acrylonitrile, butadiene and styrene (ABS), polyurethanes, polyamides, polyesters, polyolefins and of surface coatings.

Particularly effective stabilization of polyurethanes is achieved when the polyurethane is stabilized with a mixture of at least one compound I, at least one of the abovementioned antioxidants and at least one of the abovementioned sterically hindered amines.

The esters and amides of aminomethylenecyanoacetic acid I according to the invention are also suitable as sunscreen agents in cosmetic preparations, ie. in particular for the protection of the human skin from the injurious action of light, specifically sunlight, but also artificial light which has a high UV content. Thus, organic materials are to be understood in the widest sense as including the human skin. The cosmetic preparations as such are, of course, also stabilized in order to remain effective for as long as possible.

Accordingly, the present invention also relates to cosmetic preparations which contain from 0.1 to 10% by weight, preferably 1 to 7% by weight, based on the amount of the cosmetic preparation, of one or more esters and amides of aminomethylenecyanoacetic acid I as sunscreen agents. Examples of cosmetic preparations of this type are sunscreen products in liquid, solid or pasty form such as creams, lotions, aerosol foam creams, gels, oils, grease pencils, dusting powders or sprays.

The compounds I are used in the cosmetic preparations in the conventional vehicles or diluents, for example as solution in a cosmetic oil. Examples of conventional cosmetic oil components are liquid paraffin, glyceryl stearate, isopropyl myristate, diisopropyl adipate, cetylstearyl 2-ethylhexanoate, hydrogenated polyisobutene, petrolatum, caprylic/capric acid triglycerides, microcrystalline wax, lanolin and stearic acid. The good solubility of the compounds I in these oil components is a particular advantage.

The compounds I according to the invention are very compatible with the conventional types of plastics and have high solubility in the conventional coating systems and the conventional cosmetic oils. As a rule, they have little or no intrinsic color, are stable and involatile at the conventional processing temperatures for plastics and surface coatings, show only a slight tendency to migrate and, above all, provide long-lasting protection of the organic materials treated with them.

PREPARATION EXAMPLES

EXAMPLE 1

21.0 g (0.10 mol) of 1,3-propanediol dicyanoacetate, 19.6 g (0.21 mol) of aniline and 34.1 g (0.23 mol) of triethyl orthoformate in 50 ml of ethylene glycol were heated at 110° C. for 2 h. 38 ml of ethanol were slowly distilled out, during which the temperature rose to 140° C. The mixture was then cooled to 80° C., 100 ml of methanol were added and the mixture was cooled to room temperature. The precipitate was filtered off and washed with methanol and was further purified by boiling with methanol. 27.3 g of product (corresponding to a yield of 66%) of melting point 164°–166° C. were obtained.

The spectroscopic data are shown in Table 1.

EXAMPLES 2 TO 57

The products of cyanoacetic esters II and triethyl orthoformate shown in Table 1 were prepared in a similar manner to Example 1 using the appropriate aromatic or heteroaromatic amines $R^1$—$NH_2$ or $R^2$—$NH_2$. The melting points and the spectroscopic data of the products are likewise given in Table 1.

TABLE 1

Structure, melting point and spectroscopic data for the aminomethylenecyanoacetic esters I prepared

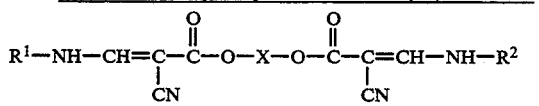 (I)

| Ex. No. | $R^1$ | $R^2$ | X | Melting point [°C.] | UV data ($CH_2Cl_2$) $\lambda_{max}$ [nm] | $\epsilon$ |
|---|---|---|---|---|---|---|
| $R^1$, $R^2$ = phenyl substituted by the following groups: | | | | | | |
| 1 | H | H | $(CH_2)_3$ | 164–66 | 321 | 53800 |
| 2 | 4-$COOC_2H_5$ | 4-$COOC_2H_5$ | $(CH_2)_3$ | 228–30 | 333 | 79800 |
| 3 | 3-$CH_3$ 5-$CH_3$ | 3-$CH_3$ 5-$CH_3$ | $(CH_2)_3$ | 246–48 | 324 | 34200 |
| 4 | 2-$CH_3$ 4-$CH_3$ | 2-$CH_3$ 4-$CH_3$ | $(CH_2)_3$ | 185 | 330 | 46900 |
| 5 | 4-$CH_3$ | 4-$CH_3$ | $(CH_2)_3$ | 186 | 326 | 51400 |
| 6 | 4-$OCH_3$ | 4-$OCH_3$ | $(CH_2)_3$ | 189 | 333 | 45400 |
| 7 | 4-$OCH_3$ | 2-$CH_3$ 4-$OCH_3$ | $(CH_2)_3$ | 175 | 335 | 41400 |
| 8 | H | H | $(CH_2)_2$ | 219 | 323 | 51700 |
| 9 | 4-$COOC_2H_5$ | 4-$COOC_2H_5$ | $(CH_2)_2$ | 246–48 | 330 | |
| 10 | 3-$CH_3$ 5-$CH_3$ | 3-$CH_3$ 5-$CH_3$ | $(CH_2)_2$ | 225–28 | 325 | 49500 |
| 11 | 2-$CH_3$ 4-$CH_3$ | 2-$CH_3$ 4-$CH_3$ | $(CH_2)_2$ | 222 | 331 | 44300 |
| 12 | 4-$CH_3$ | 4-$CH_3$ | $(CH_2)_2$ | 260 | 327 | 51900 |
| 13 | 4-$OCH_3$ | 4-$OCH_3$ | $(CH_2)_2$ | 262 | 332 | |
| 14 | 3-$CH_3$ 4-$OCH_3$ | 2-$CH_3$ 4-$OCH_3$ | $(CH_2)_2$ | 220 | 335 | 37800 |
| 15 | H | H | $(CH_2)_4$ | 189 | 321 | 51200 |
| 16 | 4-$COOC_2H_5$ | 4-$COOC_2H_5$ | $(CH_2)_4$ | 246 | 334 | 64600 |
| 17 | 4-$CH_3$ | 4-$CH_3$ | $(CH_2)_4$ | 212 | 327 | 52200 |
| 18 | 2-$CH_3$ 4-$CH_3$ | 2-$CH_3$ 4-$CH_3$ | $(CH_2)_4$ | 226 | 331 | 46500 |
| 19 | 4-$OCH_3$ | 4-$OCH_3$ | $(CH_2)_4$ | 219 | 332 | 45300 |
| 20 | 3-$CH_3$ 5-$CH_3$ | 3-$CH_3$ 4-$CH_3$ | $(CH_2)_4$ | 239 | 324 | 52500 |
| 21 | H | H | $(CH_2)_6$ | 145 | 321 | 54900 |
| 22 | 4-$COOC_2H_5$ | 4-$COOC_2H_5$ | $(CH_2)_6$ | 232 | 333 | 77700 |
| 23 | 3-$CH_3$ 5-$CH_3$ | 3-$CH_3$ 5-$CH_3$ | $(CH_2)_6$ | 188 | 324 | 53000 |
| 24 | 2-$CH_3$ 4-$CH_3$ | 2-$CH_3$ 4-$CH_3$ | $(CH_2)_6$ | 223 | 330 | 44900 |
| 25 | 4-$CH_3$ | 4-$CH_3$ | $(CH_2)_6$ | 193 | 323 | 50700 |
| 26 | 4-$OCH_3$ | 4-$OCH_3$ | $(CH_2)_6$ | 163 | 331 | 45800 |
| 27 | 4-Cl | 4-Cl | $(CH_2)_6$ | 191 | 324 | 46200 |
| 28 | 4-CN | 4-CN | $(CH_2)_6$ | 268–71 | 330 | |
| 29 | H | H | 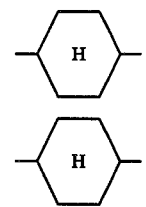 | 255–64 | 324 | 62700 |
| 30 | 4-$OCH_3$ | 4-$OCH_3$ | 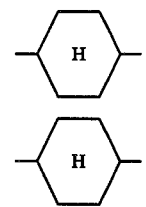 | 265 | 333 | 44800 |

TABLE 1-continued

Structure, melting point and spectroscopic data for the aminomethylenecyanoacetic esters I prepared $$R^1-NH-CH=C(CN)-C(=O)-O-X-O-C(=O)-C(CN)=CH-NH-R^2 \quad (I)$$

| Ex. No. | R¹ | R² | X | Melting point [°C.] | UV data (CH₂Cl₂) λ_max [nm] | ε |
|---|---|---|---|---|---|---|
| 31 | 3-COOC₂H₅ | 4-COOC₂H₅ | cyclohexyl-1,4 | 239–47 | 336 | 81700 |
| 32 | 3-CH₃ | 3-CH₃ | cyclohexyl-1,4 | 259–64 | 325 | 51200 |
| 33 | 5-CH₃, 2-CH₃ | 5-CH₃, 2-CH₃ | cyclohexyl-1,4 | 247 | 332 | 48400 |
| 34 | 4-CH₃ | 4-CH₃ | cyclohexyl-1,4 | 280 | 326 | 53500 |
| 35 | 5-CN | 4-CN | cyclohexyl-1,4 | 310 | 334 | 61700 |
| 36 | H | H | cyclohexyl-1,4 | 113 | 320 | 49700 |
| 37 | H | H | CH₂—CH=CH—CH₂ | 139 | 322 | 54400 |
| 38 | 4-COOC₂H₅ | 4-COOC₂H₅ | CH₂—CH=CH—CH₂ | 183 | 332 | 77400 |
| 39 | 3-CH₃, 5-CH₃ | 3-CH₃, 5-CH₃ | CH₂—CH=CH—CH₂ | 137 | 325 | 52400 |
| 40 | 2-CH₃, 4-CH₃ | 2-CH₃, 4-CH₃ | CH₂—CH=CH—CH₂ | 206 | 330 | 48600 |
| 41 | 4-CH₃ | 4-CH₃ | CH₂—CH=CH—CH₂ | 184 | 326 | 52700 |
| 42 | 4-Cl | 4-Cl | CH₂—CH=CH—CH₂ | 213 | 326 | 59700 |
| 43 | H | H | CH₂—C≡C—CH₂ | 185 | 322 | 52400 |
| 44 | 4-COOC₂H₅ | 4-COOC₂H₅ | CH₂—C≡C—CH₂ | 242 | 332 | 79100 |
| 45 | 3-CH₃, 5-CH₃ | 3-CH₃, 5-CH₃ | CH₂—C≡C—CH₂ | 239 | 324 | |
| 46 | 2-CH₃, 4-CH₃ | 2-CH₃, 4-CH₃ | CH₂—C≡C—CH₂ | 249 | 331 | 45000 |
| 47 | 4-CH₃ | 4-CH₃ | CH₂—C≡C—CH₂ | 244 | 327 | 50500 |
| 48 | 4-Cl | 4-Cl | CH₂—C≡C—CH₂ | 243 | 326 | 54600 |
| 49 | 2-CH₃ | 2-CH₃ | (CH₂)₆ | 205 | 328 | 48500 |
| 50 | H | H | CH₂—(cyclohexyl-1,4)—CH₂ | 257 | 320 | |
| 51 | 4-COOC₂H₅ | 4-COOC₂H₅ | CH₂—(cyclohexyl-1,4)—CH₂ | 263 | 329 | |
| 52 | 2-OCH₃, 4-OCH₃ | 2-OCH₃, 4-OCH₃ | (CH₂)₆ | 242–45 | 348 | |
| 53 | H | H | (CH₂CH₂O)₄,₂—CH₂CH₂ | (resin) | 321 | |

R¹—R² = Hetaryl

| Ex. No. | | | X | Melting point [°C.] | λ_max [nm] | ε |
|---|---|---|---|---|---|---|
| 54 | 3-Pyridinyl | | (CH₂)₂ | 200 | 318 | |
| 55 | 4,6-Dimethyl-2-pyrimidinyl | | (CH₂)₂ | 228 | 316 | 63400 |

TABLE 1-continued

Structure, melting point and spectroscopic data for the aminomethylenecyanoacetic esters I prepared $$R^1-NH-CH=\underset{CN}{C}-\overset{O}{\underset{\|}{C}}-O-X-O-\overset{O}{\underset{\|}{C}}-\underset{CN}{C}=CH-NH-R^2 \quad (I)$$

| Ex. No. | Structure R¹ | R² | X | Melting point [°C.] | UV data (CH$_2$Cl$_2$) $\lambda_{max}$ [nm] | $\epsilon$ |
|---|---|---|---|---|---|---|
| 56 | 4,6-Dimethyl-2-pyrimidinyl | | ⟨H⟩ (1,4-cyclohexylene) | 262–65 | 315 | 71700 |
| 57 | 4,6-Dimethyl-2-pyrimidinyl | | (CH$_2$)$_4$ | 203 | 314 | 64800 |

Note: The double bond in 1,4-but-2-enylene for X in Examples Nos. 37 to 42 is cis.

EXAMPLES 58 TO 80

In a similar manner to Example 1 and using the appropriate aromatic or heteroaromatic amines R¹—NH$_2$ or R²—NH$_2$, the products listed in Table 2 were prepared from appropriate biscyanoacetamides II and triethyl orthoformate. The melting points and spectroscopic data of the products are likewise indicated in Table 2.

TABLE 2

Structure, melting point and spectroscopic data for the aminomethylenecyanoicetamides I prepared $$R^1-NH-CH=\underset{CN}{C}-\overset{O}{\underset{\|}{C}}-NH-X-NH-\overset{O}{\underset{\|}{C}}-\underset{CN}{C}=CH-NH-R^2 \quad (I)$$

| Ex. No. | Structure R¹—R² | X | Melting point [°C.] | UV data (CH$_2$Cl$_2$) $\lambda_{max}$ [nm] | $\epsilon$ |
|---|---|---|---|---|---|
| 58 | Phenyl | (CH$_2$)$_6$ | 202 | 323 | 57500 |
| 59 | 3,5-Dimethylphenyl | (CH$_2$)$_6$ | 233 | 326 | 57800 |
| 60 | 4-Ethoxycarbonylphenyl | (CH$_2$)$_6$ | | | |
| 61 | 4-Methoxyphenyl | (CH$_2$)$_6$ | 215 | 332 | 48600 |
| 62 | 4-Methylphenyl | (CH$_2$)$_6$ | 210 | 326 | 54100 |
| 63 | 2,4-Dimethylphenyl | (CH$_2$)$_6$ | 198 | 330 | 51000 |
| 64 | Phenyl | ⟨H⟩ (1,4-cyclohexylene) | 306 | 327 | 53300 |
| 65 | 4-Methylphenyl | ⟨H⟩ (1,4-cyclohexylene) | 293 | 329 | 60100 |
| 66 | 4-Methoxyphenyl | ⟨H⟩ (1,4-cyclohexylene) | 295 | 334 | 50500 |
| 67 | 3,5-Dimethylphenyl | ⟨H⟩ (1,4-cyclohexylene) | 265 | 327 | 49400 |
| 68 | Phenyl | CH$_2$—⟨H⟩—CH$_2$ | 218 | 324 | 54000 |

TABLE 2-continued

Structure, melting point and spectroscopic data
for the aminomethylenecyanoicetamides I prepared $$R^1-NH-CH=\underset{CN}{C}-\underset{O}{\overset{\parallel}{C}}-NH-X-NH-\overset{O}{\overset{\parallel}{C}}-\underset{CN}{C}=CH-NH-R^2 \quad (I)$$

| Ex. No. | Structure R¹—R² | X | Melting point [°C.] | UV data (CH₂Cl₂) λ$_{max}$ [nm] | ε |
|---|---|---|---|---|---|
| 69 | 4-Ethoxycarbonyl-phenyl | CH₂—⟨H⟩—CH₂ | 271 | 337 | 83600 |
| 70 | 4-Methoxyphenyl | CH₂—⟨H⟩—CH₂ | 246 | 332 | 46300 |
| 71 | Phenyl | (CH₂)₂ | 268 | 325 | 56100 |
| 72 | 4-Ethoxycarbonyl-phenyl | (CH₂)₂ | 235 | 337 | 73200 |
| 73 | 3,5-Dimethylphenyl | (CH₂)₂ | 261 | 327 | 56300 |
| 74 | 4-Methylphenyl | (CH₂)₂ | 263 | 328 | 57200 |
| 75 | 4-Methoxyphenyl | (CH₂)₂ | 244 | 333 | — |
| 76 | 4,6-Dimethyl-2-pyrimidinyl | (CH₂)₇ | 263 | 315 | 71500 |
| 77 | 4,6-Dimethyl-2-pyrimidinyl | —⟨H⟩— | 311 | 315 | — |
| 78 | Phenyl | (CH₂)₃ | 203 | 324 | 58400 |
| 79 | 4-Methylphenyl | (CH₂)₃ | 231 | 328 | 58600 |
| 80 | 4-Methoxyphenyl | (CH₂)₃ | 191 | 333 | 51000 |

USE EXAMPLES

ABS specimens for the light exposure tests were produced by dissolving 0.5% by weight of the sterically hindered amine of the formula IV and 0.5% by weight of the UV absorber according to the invention which is indicated in Table 3 in ABS (Terluran 967 K, unpigmented) by a single extrusion at a melt temperature of 250° C., and injection molding the resulting granules at 260° C. to give specimens 2 mm thick.

The specimens were tested for resistance to light and weathering in a Xenotest• 1200 accelerated weathering tester.

The yellowness index (YI, Annual Book of ASTM Standards D 1925-70 (Reapproved 1977)) is a measure of the photooxidative breakdown of the polymer during the weathering time.

The stabilizer mixtures used, and the results of the light exposure test are detailed in Table 3.

TABLE 3

| YI values for ABS specimens | |
|---|---|
| Stabilzer mixture | YI after 500 h |
| According to the invention: | |
| 0.5% by wt IV + 0.5% by wt prod. of Ex. 6 | 28 |
| 0.5% by wt IV + 0.5% by wt prod. of Ex. 15 | 27 |
| 0.5% by wt IV + 0.5% by wt prod. of Ex. 17 | 28 |
| Comparative: | |
| No stabiliser | 52 |
| 0.5% by wt IV + 0.5% by wt IIIa | 34 |

TABLE 3-continued

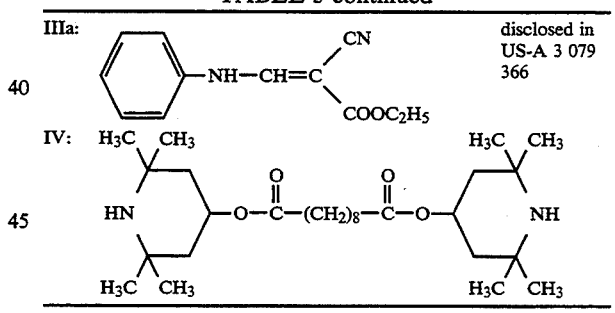

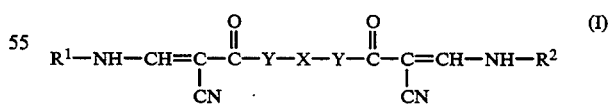

We claim:

1. An ester or amide of aminomethylenecyanoacetic acid of the formula I $$R^1-NH-CH=\underset{CN}{C}-\overset{O}{\overset{\parallel}{C}}-Y-X-Y-\overset{O}{\overset{\parallel}{C}}-\underset{CN}{C}=CH-NH-R^2 \quad (I)$$

where R¹ and R² are each, independently of one another, phenyl, naphthyl, biphenylyl, pyridine or pyrimidine, it being possible for these radicals to be substituted by one to three C₁–C₁₂-alkyl groups, C₁–C₁₂-alkoxy groups, halogen atoms, cyano groups, hydroxyl groups or groups of the formulae COOR³, COR³, CONHR³, OCOR³ or NHCOR³, and where R³ is C₁–C₁₂-alkyl, C₅–C₈-cycloalkyl or phenyl, X is C₂–C₃₀-alkylene which can be interrupted by non-adjacent oxygens, or is C₄–C₁₂-alkenylene or $C_4$–$C_{12}$-alkynylene where the unsaturated bonds are not adjacent to the ester oxygens, or is $C_5$–$C_8$-cycloalkylene or phenylene, and Y is O or NH.

2. An ester or amide of aminomethylenecyanoacetic acid I as claimed in claim 1, where $R^1$ and $R^2$ are each, independently of one another, phenyl which can be substituted by one or two $C_1$–$C_{12}$-alkyl groups, $C_1$–$C_{12}$-alkoxy groups, chlorine atoms, cyano groups, hydroxyl groups or groups of the formula $COOR^3$ or pyridinyl or 2-pyrimidinyl, each of which can be substituted by one or two $C_1$–$C_4$-alkyl groups.

3. An ester or amide of aminomethylenecyanoacetic acid I as claimed in claim 1 or 2, where X is $C_2$–$C_{12}$-alkylene, —$(CH_2CH_2O)_n$—$CH_2CH_2$— or

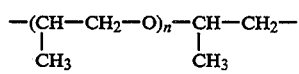

where n is 1 to 9, 1,4-but-2-enylene, 1,4-but-2-ynylene, $C_6$–$C_8$-cycloalkylene or phenylene.

4. The ester or amide of claim 1, wherein $R^1$ and $R^2$ are each independently selected from the group consisting of phenyl, naphthyl, biphenylyl, pyridine and pyrimidine each of which are unsubstituted.

5. The ester or amide of claim 4, wherein $R^1$ and $R^2$ are each independently phenyl, pyridyl or pyrimidyl.

6. The ester or amide of claim 4, wherein $R^1$ and $R^2$ are the same.

7. A cosmetic preparation containing from 0.1 to 10% by weight, based on the amount of the cosmetic preparation, of one or more esters or amides of aminomethylenecyanoacetic acids I as claimed in claim 1, 2, 3 or 4.

8. A method for protecting human skin from the action of light, which comprises applying to said human skin a cosmetic preparation comprising one or more esters or amides of aminomethylenecyanoacetic acid I as claimed in claim 1, 2, 3 or 4 in an amount effective as a sunscreen agent.

* * * * *